United States Patent
Simeone et al.

(10) Patent No.: US 9,700,541 B2
(45) Date of Patent: Jul. 11, 2017

(54) SEIZURE THERAPY

(71) Applicant: Creighton University, Omaha, NE (US)

(72) Inventors: Kristina A. Simeone, Omaha, NE (US); Timothy A. Simeone, Omaha, NE (US)

(73) Assignee: Creighton University, Omaha, NE (US)

( * ) Notice: Subject to any disclaimer, the term of this patent is extended or adjusted under 35 U.S.C. 154(b) by 0 days.

(21) Appl. No.: 14/405,816

(22) PCT Filed: Jun. 12, 2013

(86) PCT No.: PCT/US2013/045355
§ 371 (c)(1),
(2) Date: Dec. 5, 2014

(87) PCT Pub. No.: WO2013/188509
PCT Pub. Date: Dec. 19, 2013

(65) Prior Publication Data
US 2015/0164857 A1    Jun. 18, 2015

Related U.S. Application Data

(60) Provisional application No. 61/660,207, filed on Jun. 15, 2012.

(51) Int. Cl.
*A61K 31/355* (2006.01)
*A61K 31/375* (2006.01)
*A61K 31/19* (2006.01)

(52) U.S. Cl.
CPC ............ *A61K 31/355* (2013.01); *A61K 31/19* (2013.01); *A61K 31/375* (2013.01)

(58) Field of Classification Search
None
See application file for complete search history.

(56) References Cited

FOREIGN PATENT DOCUMENTS

WO          9316690        9/1993
WO      WO 9316690 A1 *   9/1993    ............ A61K 8/361

OTHER PUBLICATIONS

Itala Monica Sales Santos, Adriana Da Rocha Tome; Glaucio Barros Saldanha, Paulo Michel Pinheiro Ferreira, Gardenia Carmem Gadelha Militao, and Rivelilson Mendes De Freitas; "Oxidative stress in the hippocampus during experimental seizures can be ameliorated with the antioxidant ascorbic acid"; Oxidative Medicine and Cellular Longevity; 2009; vol. 2, Issue 4; pp. 214-221.
Angel Barbel-Garcia, Jose Ramon Barbera-Farre, Jesus Porta Etessam, Antonio Martinez Salio, Ana Cabello, Eduardo Gutierrez-Rivas, and Yolanda Campos; "Coenzyme Q 10 Improves Lactic Acidosis, Strokelike Episodes, and Epilepsy in a Patient with MELAS (Mitochondrial Myopathy, Encephalopathy, Lactic Acidosis, and Strokelike episodes)", Clinical Neuropharmacology; 2004; vol. 27, Issue 4; pp. 187-191.
Vytautas P. Bindokas, Chong C. Lee, William F. Colmers, and Richard J. Miller; "Changes in Mitochondrial Function Resulting from Synaptic Activity in the Rat Hippocampal Slice"; 1998; vol. 18, Issue 12; pp. 4570-4587.
John M. Shoffner, Marie T. Lott, Angela M. S. Lezza, Peter Seibel, Scott W. Ballinger, and Douglas C. Wallace; "Myoclonic Epilepsy and Ragged-Red Fiber Disease (MERRF) is Associated with a Mitochondrial DNA rRNAlys Mutation"; 1990; vol. 61; pp. 931-937.

* cited by examiner

*Primary Examiner* — Heidi Reese
(74) *Attorney, Agent, or Firm* — Advent, LLP (57) ABSTRACT

A method and a composition are utilized to affect mitochondrial functions on a seizure-genic brain region. In one aspect, the disclosure comprises methods of treating seizures. Seizures are a transient symptom of abnormal excessive or synchronous neuronal activity in the brain. Seizures may manifest as a wild thrashing movement, a brief loss of awareness, an alteration in mental state, tonic or clonic movements, convulsions, a full body slump, and various other psychic symptoms such as déjà vu or jamais vu. Recurrent, unprovoked seizures are medically known as epilepsy. In one implementation, the method of treating a seizure includes administering a composition that restores mitochondrial function to a seizure-genic brain region. In some embodiments, the composition can include ascorbic acid, vitamin E, and pyruvate.

17 Claims, 12 Drawing Sheets

SEIZURE THERAPY

BACKGROUND

Epilepsy is a neurological disorder defined by recurrent spontaneous seizures. Approximately 1% of people in the US have epilepsy. Seizures are associated with cell toxicity, hyperexcitability and death. Anti-epileptic drugs act primarily on ion channels and receptors for calcium, sodium, potassium, glutamate and GABA. Current FDA approved anti-epileptic drugs that target these pathways fail to control seizures in 30% of patients.

SUMMARY

In one aspect, the disclosure comprises methods of treating seizures. Seizures are a transient symptom of abnormal excessive or synchronous neuronal activity in the brain. Seizures may manifest as a wild thrashing movement, a brief loss of awareness, an alteration in mental state, tonic or clonic movements, convulsions, a full body slump, and various other psychic symptoms such as déjà vu or jamais vu. Recurrent, unprovoked seizures are medically known as epilepsy.

In one implementation, the method of treating a seizure includes administering a composition that restores mitochondrial function to a seizure-genic brain region. In another implementation, the method of treating a seizure includes administering a composition that restores mitochondrial function to a seizure-genic brain region, wherein the composition is administered to a subject suffering from seizure. In another implementation, the method of treating a seizure includes administering a composition that restores mitochondrial function to a seizure-genic brain region, wherein the composition is administered to a subject suffering from seizure. In another implementation, the method of treating a seizure includes administering a composition that restores mitochondrial function in a brain region, wherein the composition is administered to a subject unable or unwilling to abide by a ketogenic diet or any other dietary or pharmaceutical anticonvulsant treatment. In another implementation, the method of treating a seizure includes administering a composition that impairs mitochondrial function to a seizure-genic brain region. In some embodiments, the composition can include ascorbic acid, vitamin E, and pyruvate. In one specific embodiment, the composition includes a combination of acorbic acid, pyruvate, and tocopherol, wherein the ratio of ascorbic acid to tocopherol is between about 1:6 and about 1:10, the ratio of ascorbic acid to pyruvate is between about 1:1.5 and about 1:4.5, and the ratio of tocopherol to pyruvate is between about 1:12 and about 1:40.

This Summary is provided to introduce a selection of concepts in a simplified form that are further described below in the Detailed Description. This Summary is not intended to identify key and/or essential features of the claimed subject matter. Also, this Summary is not intended to limit the scope of the claimed subject matter in any manner. Aspects of the disclosure pertain to methods and compositions for treating seizures.

BRIEF DESCRIPTION OF THE FIGURES

FIG. 5A depicts electrophysiological recordings showing inhibition of mitochondrial complex I of the electron transport chain creates a hyperexcitable environment in acute mouse hippocampal slices. Epilepsy is defined as a neuronal state of hyperexcitability and hypersynchrony. Extracellular recordings in the CA3 stratum radiatum reveals that a 30 min application of the mitochondrial complex I inhibitor rotenone (100 nM) increases the rate and amplitudes of spontaneous field potentials. The middle trace is an expansion of field potential marked by an asterisk in the top trace. Time-frequency analysis was performed on the signals to examine the component frequencies occurring during the field potentials. High frequency oscillations (HF05) in the 100-200 Hz bandwidth (called ripples) are normal and reflect small clusters of neurons firing action potentials synchronously. Rotenone application results in spectral disorganization and the generation of faster HFOs (called fast ripples) which reflects a desynchronization of neuronal firing. Fast ripples occur in humans and animals with epilepsy and are biomarkers for seizure-genic foci.

FIG. 5B (Right) shows that applying rotenone the intensity of ripples and fast ripples increases in the slices. Following application of high potassium, the seizure-like events are greater in amplitude and longer in duration, indicating greater seizure severity during mitochondrial dysfunction.

FIG. 6A shows a representative EEG trace of tonic-clonic seizures.

FIG. 7A is a double-plotted bar graph and scatterplot depicting the antiepileptogenic effects of AATP treatment. Young Kv1.1−/− mice (~P22-P26) were continuously monitored for 48 hrs to establish a baseline seizure frequency and severity score for each animal. AATP treatment was then administered daily for 5 days, supplemented in their diet, and was followed by a 48 hr washout period (ascorbic acid, ~570 mg/kg; sodium pyruvate, ~2100 mg/kg; tocopherol-succinate, ~70 mg/kg). AATP diet treatment significantly reduced seizure frequency and severity when compared within groups (to pretreatment baseline scores) and between treated and age-matched controls. In addition, these effects persisted following discontinuation of treatment (washout).

FIGS. 7B-C shows that AATP is anticonvulsant in severe status epilepticus. Mice underwent microneurosurgery and were implanted with subdural electroencephalographic (EEG) electrodes. Following a 5-7 day recovery, mice were pretreated with AATP (ascorbic acid, 250 mg/kg; sodium pyruvate, 500 mg/kg; tocopherol-succinate, 30 mg/kg, i.p. injection). Thirty min later, the proconvulsant kainic acid (10 mg/kg, i.p.) was administered to induce status epilepticus. Electroencephalographic and behavioral seizures were continuously monitored and scored for 3 hrs; *p<0.05.

DETAILED DESCRIPTION

In one aspect, the disclosure comprises methods of treating seizures. Seizures are a transient symptom of abnormal excessive or synchronous neuronal activity in the brain. Seizures may manifest as a wild thrashing movement, a brief loss of awareness, an alteration in mental state, tonic or clonic movements, convulsions, a full body slump, and various other psychic symptoms such as déjà vu or jamais vu. Recurrent, unprovoked seizures are medically known as epilepsy.

As more fully set forth herein impaired mitochondrial function is associated with seizure-genesis. This disclosure pertains to a composition that restores mitochondrial respiratory, antioxidant, and uncoupling functions in order to treat seizure. The composition may treat refractory seizures that are not treated by current seizure medicines and dietary regimens used to treat refractory seizure. In some instances, seizures may cause neuronal damage. As such, aspects of the disclosure also pertain to protection from neuronal damage by preventing seizures.

(a) Seizure

This disclosure describes a method of treating seizure. Non limiting examples of seizures that may be treated by the composition may include seizures that occur in benign Rolandic epilepsy, frontal lobe epilepsy, infantile spasms, juvenile myoclonic epilepsy, juvenile absence epilepsy, childhood absence epilepsy (pyknolepsy), hot water epilepsy, Lennox-Gastaut syndrome, Landau-Kleffner syndrome, Dravet syndrome, progressive myoclonus epilepsies, reflex epilepsy, Rasmussen's syndrome, temporal lobe epilepsy, limbic epilepsy, status epilepticus, abdominal epilepsy, massive bilateral myoclonus, catamenial epilepsy, Jacksonian seizure disorder, Lafora disease, photosensitive epilepsy, and epilepsy induced by chemoconvulsant. In nonhuman animals, chemoconvulsants may be kainate acid (KA), Pentylenetetrazole (PTZ), lithium pilocarpine, electroconvulsive shocks, vagal nerve stimulation, high frequency stimulation or kindling, and N-methyl-D-aspartate.

The method may treat seizures that occur in status epilepticus. Status epilepticus is a life-threatening condition in which the brain is in a state of persistent seizure lasting at least 1 hour, or recurrent seizures without regaining consciousness between seizures for at least 1 hour.

Treating seizures may comprise reducing seizure intensity, reducing seizure frequency, reducing epileptogenesis or a combination thereof. As used herein, the term "epileptogenesis" may be a gradual process by which a normal brain develops epilepsy resulting from acute brain insults such as traumatic brain injury, stroke, idiopathic ontogeny, or infection. In epileptogenesis, an array of events occur on molecular and cellular levels that cause neurons to fire in a disordered manner, resulting in seizures.

In some embodiments, treating seizure reduces seizure intensity. In other embodiments, treating seizure reduces seizure frequency. In yet other embodiments, treating seizures may comprise reducing epileptogenesis. In some embodiments, treating seizure reduces seizure intensity and epileptogenesis. In other embodiments, treating seizure reduces seizure frequency and epileptogenesis. In yet other embodiments, treating seizures reduces seizure frequency and seizure intensity. In other embodiments, treating seizures reduces seizure frequency, seizure intensity, and epileptogenesis.

Methods of measuring seizure intensity and frequency may include behavioral scoring, electroencephalography (EEG), electrocorticography (ECoG), electromyography (EMG), electrocardiography (EKG), fMRI, MRI or a combination thereof. In some embodiments, seizure intensity and frequency is measured using EEG. In other embodiments, seizure intensity and frequency is measured using behavioral scoring. Non limiting examples of behavioral scoring methods for measuring seizure intensity and frequency may include the Denver seizure score, the Racine scale, Luttjohann method, and the modified Racine scale. In some embodiments, seizure intensity and frequency is measured using the modified Racine scale for behavioral scoring as described in the examples. The modified Racine scale may be used to score seizure intensity as follows: 1, immobility; 2, forelimb and/or tail extension; rigid posture; 3, repetitive movements; head bobbing; 4, rearing and falling; 5, continuous rearing and falling; 6, severe tonic clonic seizures In one embodiment, a method treats seizure by restoring mitochondrial function in seizure-genic brain regions. As used herein, the term "seizure-genic brain region" may be any region of the brain where mitochondrial function may be impaired, leading to a seizure. For instance, seizures may originate from an epileptic focus where mitochondrial function is impaired, a small portion of the brain that serves as the irritant driving the epileptic response. Seizures may also originate from many independent foci (multifocal epilepsies) where mitochondrial function may be impaired, or from epileptic circuits that involve the whole brain or whole regions of the brain where mitochondrial function may be impaired. In some embodiments, the seizure-genic region of the brain is an epileptic focus in the brain where mitochondrial function may be impaired. In other embodiments, the seizure-genic region of the brain is from epileptic circuits that involve the whole brain or whole regions of the brain where mitochondrial function may be impaired.

A seizure-genic brain region may be any region of the brain where seizures may occur. Non limiting examples of a seizure-genic brain region may include the cortex, the hippocampus, the amygdala, the medulla, the pons, the thalamus, the cerebellum, the optic tectum, the pallium, the basal ganglia, the olfactory bulb, and the parahippocampal gyrus. In some embodiments, the seizure-genic brain region may be the hippocampus. In other embodiments, the seizure-genic brain region may be the cortex.

The method may be used to treat refractory seizures. As used herein, the term "refractory seizure" may be used to describe any seizures that do not come under control with established methods of controlling seizures. Non limiting examples of methods of controlling seizures may include medicines or diet changes. In some embodiments, the method of the invention may be used to treat refractory seizures that do not come under control with seizure medication. Non limiting examples of seizure medication may include anticonvulsants such as albutoin; Ameltolide; atolide; buramate; cinromide; citenamide; clonazepam; cyheptamide; dezinamide; dimethadione; divalproex sodium; eterobarb; ethosuximide; ethotoin; flurazepam hydrochloride; fluzinamide; fosphenyloin sodium; gabapentin; ilepcimide; lamotrigine; magnesium sulfate; mephenyloin; mephobarbital; methetoin; methsuximide; milacemide hydrochloride; nabazenil; nafimidone hydrochloride; nitrazepam; phenacemide; phenobarbital; phenobarbital sodium; phensuximide; phenyloin; phenyloin sodium; primidone; progabide; ralitoline; remacemide hydrochloride; ropizine; sabeluzole; stiripentol; sulthiame; topiramate; trimethadione; valproate sodium; valproic acid; vigabatrin; zoniclezole hydrochloride; and zonisamide, and an antiepileptic such as felbanate; iamotrigine; loreclezole; tolgabide.

In other embodiments, the method may be used to treat refractory seizures that do not come under control with diet changes. Non-limiting examples of diet changes may include a ketogenic diet. The ketogenic diet is a high-fat, adequate-protein, low-carbohydrate diet used primarily to treat refractory epilepsy. Refractory seizures may not come under control with diet change such as a ketogenic diet because the subject may not be able to abide by the ketogenic diet. For instance the subject may not be able to abide by the ketogenic diet because of complicated administration regimens, palatability issues, and possible side effects due to high fat content. In some embodiments, the composition may be administered to a subject unable to abide by the ketogenic diet.

Treating seizure using the method may reduce seizure frequency and intensity as measured by a seizure score. In some embodiments, seizure severity may be reduced by about 30, 35, 40, 45, 50, 55, 60, 65, 70, 75, 80, 85, 90, 95, or about 100%. In other embodiments, seizure severity may be reduced by about 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or about 60%. In yet other embodiments, seizure severity may be reduced by about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or about 80%. In still other embodiments, seizure severity may be reduced by about 70, 71, 72, 73, 74, 75, 76, 77, 78, 79, 80, 81, 82, 83, 84, 85, 86, 87, 88, 89, 90, 91, 92, 93, 94, 95, or about 100%.

In some embodiments, seizure intensity may be reduced by about 30, 35, 40, 45, 50, 55, 60, 65, 70, 75, 80, 85, 90, 95, or about 100%. In other embodiments, seizure intensity may be reduced by about 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, or about 60%. In yet other embodiments, seizure intensity may be reduced by about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or about 80%. In preferred embodiments, seizure intensity may be reduced by about 70, 71, 72, 73, 74, 75, 76, 77, 78, 79, 80, 81, 82, 83, 84, 85, 86, 87, 88, 89, 90, 91, 92, 93, 94, 95, or about 100%.

(b) Composition

The method comprises administering a composition that restores mitochondrial function. The composition may comprise any compound that may restore mitochondrial function. Non limiting examples of compounds that may restore mitochondrial function may include ascorbic acid, vitamin E, pyruvate, ubiquinone, co-enzyme Q, or combinations thereof. Non limiting examples of combinations of compounds that may restore mitochondrial function may be as shown in Table A.

TABLE A

| Combinations |
|---|
| Ascorbic acid |
| Vitamin E |
| Pyruvate |
| Ubiquinone |
| Co-enzyme Q |
| Ascorbic acid, Vitamin E |
| Ascorbic acid, Pyruvate |
| Ascorbic acid, Ubiquinone |
| Ascorbic acid, Co-enzyme Q |
| Vitamin E, Pyruvate |
| Vitamin E, Ubiquinone |
| Vitamin E, Co-enzyme Q |
| Pyruvate, Ubiquinone |
| Pyruvate, Co-enzyme Q |
| Ubiquinone, Co-enzyme Q |
| Ascorbic acid, Vitamin E, Pyruvate |
| Ascorbic acid, Vitamin E, Ubiquinone |
| Ascorbic acid, Vitamin E, Co-enzyme Q |
| Ascorbic acid, Pyruvate, Ubiquinone |
| Ascorbic acid, Pyruvate, Co-enzyme Q |
| Ascorbic acid, Ubiquinone, Co-enzyme Q |
| Vitamin E, Pyruvate, Ubiquinone |
| Vitamin E, Pyruvate, Co-enzyme Q |
| Vitamin E, Ubiquinone, Co-enzyme Q |
| Pyruvate, Ubiquinone, Co-enzyme Q |
| Ascorbic acid, Vitamin E, Pyruvate, Ubiquinone |
| Ascorbic acid, Vitamin E, Pyruvate, Co-enzyme Q |
| Ascorbic acid, Vitamin E, Ubiquinone, Co-enzyme Q |
| Ascorbic acid, Pyruvate, Ubiquinone, Co-enzyme Q |
| Vitamin E, Pyruvate, Ubiquinone, Co-enzyme Q |
| Ascorbic acid, Vitamin E, Pyruvate, Ubiquinone, Co-enzyme Q |

In some embodiments, the composition comprises ascorbic acid, vitamin E, and pyruvate. Ascorbic acid is a naturally occurring organic compound with antioxidant properties and is one form of vitamin C. Pyruvic acid is an organic acid, a ketone, as well as the simplest of the alpha-keto acids. In a cell, pyruvate is the output of glycolysis, the anaerobic metabolism of glucose. A group of compounds with Vitamin E activity may include tocopherols and tocotrienols. In some embodiments, the vitamin E of the composition may be a tocopherol. Non limiting examples of tocopherols that may be used in the composition may include a-tocopherol, [3-tocopherol, ytocopherol, and A-tocopherol. In some embodiments, the vitamin E of the composition may be a tocotrienol. Non limiting examples of tocotrienols that may be used in the composition may include a-tocotrienol, [3-tocotrienol, y-tocotrienol, and A-tocotrienol. In one embodiment, the vitamin E of the composition is a-tocopherol.

The dose of ascorbic acid, vitamin E, and pyruvate can vary depending on the body weight, sex, age and/or medical condition of the subject, the severity of the seizure, the method of administration, and the duration of the treatment, as well as the species of the subject.

When administered intravenously, the dose of ascorbic acid may be about 200, 210, 220, 230, 240, 250, 260, 270, 280, 290, or about 300 mg/kg. In some embodiments, the intravenous dose of ascorbic acid may be about 200, 201, 202, 203, 204, 205, 206, 207, 208, 209, 210, 211, 212, 213, 214, 215, 216, 217, 218, 219, or about 220 mg/kg. In other embodiments, the intravenous dose of ascorbic acid may be about 210, 211, 212, 213, 214, 215, 216, 217, 218, 219, 221, 222, 223, 224, 225, 226, 227, 228, 229, or about 230 mg/kg. In yet other embodiments, the intravenous dose of ascorbic acid may be about 220, 222, 223, 224, 225, 226, 227, 228, 229, 230, 231, 232, 233, 234, 235, 236, 237, 238, 239 or about 240 mg/kg. In other embodiments, the intravenous dose of ascorbic acid may be about 230, 231, 232, 233, 234, 235, 236, 237, 238, 239, 240, 241, 242, 243, 244, 245, 246, 247, 248, 249 or about 250 mg/kg. In other embodiments, the intravenous dose of ascorbic acid may be about 250, 251, 252, 253, 254, 255, 256, 257, 258, 259, 260, 261, 262, 263, 264, 265, 266, 267, 268, 269 or about 270 mg/kg. In still other embodiments, the intravenous dose of ascorbic acid may be about 260, 261, 262, 263, 264, 265, 266, 267, 268, 269, 270, 271, 272, 273, 274, 275, 276, 277, 278, 279, or about 280 mg/kg. In yet other embodiments, the intravenous dose of ascorbic acid may be about 270, 271, 272, 273, 274, 275, 276, 277, 278, 279, 280, 281, 282, 283, 284, 285, 286, 287, 288, 289 or about 290 mg/kg. In additional embodiments, the intravenous dose of ascorbic acid may be about 280, 281, 282, 283, 284, 285, 286, 287, 288, 289, 290, 291, 292, 293, 294, 295, 296, 297, 298, 299 or about 300 mg/kg. In still other embodiments, the intravenous dose of ascorbic acid may be about 240, 241, 242, 243, 244, 245, 246, 247, 248, 249, 250, 251, 252, 253, 254, 255, 256, 257, 258, 259 or about 260 mg/kg.

When administered intraorally, the dose of ascorbic acid may be about 500, 510, 520, 530, 540, 550, 560, 570, 580, 590, 600, 610, 620, 630, 640, 650, 660, 670, 680, 690, or about 700 mg/kg. In some embodiments, the intraoral dose of ascorbic acid may be about 500, 510, 520, 530, 540, 550, 560, 570, 580, 590 or about 600 mg/kg. In other embodiments, the intraoral dose of ascorbic acid may be about 600, 610, 620, 630, 640, 650, 660, 670, 680, 690, or about 700 mg/kg. In still other embodiments, the intraoral dose of ascorbic acid may be about 550, 560, 570, 580, 590, 600, 610, 620, 630, 640 or about 650 mg/kg.

When administered intravenously, the dose of vitamin E may be about 20, 21, 22, 23, 24, 25, 26, 27, 28, 29, 30, 31, 32, 33, 34, 35, 36, 37, 38, 39 or about 40 mg/kg. In some embodiments, the intravenous dose of vitamin E may be about 20, 21, 22, 23, 24, or about 25 mg/kg. In other embodiments, the intravenous dose of vitamin E may be about 25, 26, 27, 28, 29, or about 30 mg/kg. In yet other embodiments, the intravenous dose of vitamin E may be about 30, 31, 32, 33, 34 or about 35 mg/kg. In other embodiments, the intravenous dose of vitamin may be about 35, 36, 37, 38, 39 or about 40 mg/kg. In still other embodiments, the intravenous dose of ascorbic acid may be about 25, 26, 27, 28, 29, 30, 31, 32, 33, 34 or about 35 mg/kg.

When administered intraorally, the dose of vitamin E may be about 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, 80, 81, 82, 83, 84, 85, 86, 87, 88, 89, 90, 91, 92, 93, 94, 95, 96, 97, 98, 99 or about 100 mg/kg. In some embodiments, the intraoral dose of vitamin E may be about 50, 51, 52, 53, 54, 55, 56, 57, 58, 59, 60, 61, 62, 63, 64, 65, 66, 67, 68, 69 or about 70 mg/kg. In other embodiments, the intraoral dose of vitamin E may be about 60, 61, 62, 63, 64, 65, 66, 67, 68, 69, 70, 71, 72, 73, 74, 75, 76, 77, 78, 79 or about 80 mg/kg. In yet other embodiments, the intraoral dose of vitamin E may be about 70, 71, 72, 73, 74, 75, 76, 77, 78, 79, 80, 81, 82, 83, 84, 85, 86, 87, 88, 89 or about 90 mg/kg. In other embodiments, the intraoral dose of vitamin E may be about 70, 71, 72, 73, 74, 75, 76, 77, 78, 79, 80, 81, 82, 83, 84, 85, 86, 87, 88, 89 or about 90 mg/kg. In additional embodiments, the intraoral dose of vitamin E may be about 80, 81, 82, 83, 84, 85, 86, 87, 88, 89, 90, 91, 92, 93, 94, 95, 96, 97, 98, 99 or about 100 mg/kg. In still other embodiments, the intraoral dose of vitamin E may be about 65, 66, 67, 68, 69, 70, 71, 72, 73, 74, 75, 76, 77, 78, 79, 80, 81, 82, 83, 84 or about 85 mg/kg.

When administered intravenously, the dose of pyruvate may be about 450, 460, 470, 480, 490, 500, 510, 520, 530, 540 or about 550 mg/kg. In some embodiments, the intravenous dose of pyruvate may be about 450, 451, 452, 453, 454, 455, 456, 457, 458, 459, 460, 461, 462, 463, 464, 465, 466, 467, 468, 469, or about 470 mg/kg. In other embodiments, the intravenous dose of pyruvate may be about 460, 461, 462, 463, 464, 465, 466, 467, 468, 469, 470, 471, 472, 473, 474, 475, 476, 477, 478, 479, or about 480 mg/kg. In yet other embodiments, the intravenous dose of pyruvate may be about 470, 471, 472, 473, 474, 475, 476, 477, 478, 479, 480, 481, 482, 483, 484, 485, 486, 487, 488, 489 or about 490 mg/kg. In other embodiments, the intravenous dose of pyruvate may be about 480, 481, 482, 483, 484, 485, 486, 487, 488, 489, 490, 491, 492, 493, 494, 495, 496, 497, 498, 499 or about 500 mg/kg. In other embodiments, the intravenous dose of pyruvate may be about 490, 491, 492, 493, 494, 495, 496, 497, 498, 499, 500, 501, 502, 503, 504, 505, 506, 507, 508, 509, or about 510 mg/kg. In still other embodiments, the intravenous dose of pyruvate may be about 500, 501, 502, 503, 504, 505, 506, 507, 508, 509, 510, 511, 512, 513, 514, 515, 516, 517, 518, 519, or about 520 mg/kg. In yet other embodiments, the intravenous dose of pyruvate may be about 510, 511, 512, 513, 514, 515, 516, 517, 518, 519, 520, 521, 522, 523, 524, 525, 526, 527, 528, 529 or about 530 mg/kg. In additional embodiments, the intravenous dose of pyruvate may be about 520, 521, 522, 523, 524, 525, 526, 527, 528, 529, 530, 531, 532, 533, 534, 535, 536, 537, 538, 539 or about 540 mg/kg. In still other embodiments, the intravenous dose of pyruvate may be about 530, 531, 532, 533, 534, 535, 536, 537, 538, 539, 540, 541, 542, 543, 544, 545, 546, 547, 548, 549 or about 550 mg/kg.

When administered intraorally, the dose of pyruvate may be about 1, 2, 3, 4, or about 5 g/kg. In some embodiments, the intraoral dose of pyruvate may be about 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9, 3, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9 or about 5 mg/kg. In still other embodiments, the intraoral dose of pyruvate may be about 2, 2.1, 2.2, 2.3, 2.4, 2.5, 2.6, 2.7, 2.8, 2.9, or about 3 mg/kg.

In an exemplary embodiment, 250 mg/kg ascorbic acid, 500 mg/kg pyruvate, and 30 mg/kg tocopherol are administered intravenously. In another exemplary embodiment, 600 mg/kg ascorbic acid, 2.5 g/kg pyruvate, and 75 mg/kg tocopherol are administered orally.

Administering multiple doses of the composition per day may also be used as needed to provide the desired level of seizure therapy. For instance, one, two, three, four, or more doses of the composition may be administered per day. The composition may be administered before, during or after the seizures occur. In some embodiments, the composition may be administered before the seizures occur. In other embodiments, the composition may be administered during seizures. In yet other embodiments, the composition may be administered after the seizures occur.

(c) Subject

The method comprises administering a composition to a subject. Suitable subjects may include animals and humans. Non-limiting examples of suitable animals include companion animals such as cats, dogs, rodents, and horses; research animal such as mice, rats and other rodents; agricultural animals such as cows, cattle, pigs, goats, sheep, horses, deer, chickens and other fowl; zoo animals; and primates such as chimpanzees, monkeys, and gorillas. In one embodiment, the subject is a human. In another embodiment, the subject is a human with refractory seizure. In still another embodiment, the subject is a mouse. In yet another embodiment, the subject is the Kv1.1 knockout mouse.

(d) Administration

The composition may be administered as oral, intravenous, intramuscular, subcutaneous, or parenteral routes. In some embodiments, the composition may be formulated for administration by injection (e.g., intraperitoneally, intravenously, subcutaneously, intramuscularly, etc.). Accordingly, these compositions can be combined with pharmaceutically acceptable vehicles such as saline, Ringer's solution, dextrose solution, and the like.

The composition may comprise a pharmaceutical carrier (or excipient). Such a carrier may be any solvent or solid material for encapsulation that is non-toxic. A carrier may give form or consistency, or act as a diluent. Suitable pharmaceutical carriers may include liquid carriers, such as normal saline and other non-toxic salts at or near physiological concentrations, and solid carriers not used for humans, such as talc or sucrose, or animal feed. Carriers may also include stabilizing agents, wetting and emulsifying agents, salts for varying osmolarity, encapsulating agents, buffers, and skin penetration enhancers. Carriers and excipients as well as formulations for parenteral and nonparenteral drug delivery are set forth in Remington's Pharmaceutical Sciences 19th Ed. Mack Publishing (1995).

For parenteral administration (including subcutaneous, intradermal, intravenous, intramuscular, and intraperitoneal), the composition may be an aqueous or an oil-based solution. Aqueous solutions may include a sterile diluent such as water, saline solution, a pharmaceutically acceptable polyol such as glycerol, propylene glycol, or other synthetic solvents; an antibacterial and/or antifungal agent such as benzyl alcohol, methyl paraben, chlorobutanol, phenol, thimerosal, and the like; an antioxidant such as ascorbic acid or sodium bisulfite; a chelating agent such as etheylenediaminetetraacetic acid; a buffer such as acetate, citrate, or phosphate; and/or an agent for the adjustment of tonicity such as sodium chloride, dextrose, or a polyalcohol such as mannitol or sorbitol. The pH of the aqueous solution may be adjusted with acids or bases such as hydrochloric acid or sodium hydroxide. Oil-based solutions or suspensions may further comprise sesame, peanut, olive oil, or mineral oil.

In one embodiment, the composition may be administered orally. Non-limiting examples of oral formulations that may be used to administer the amino acid composition of the invention may be a nutritional formulation, a medical food, a medical beverage, in the form of a complete meal, part of a meal, as a food additive as a powder for dissolution, in the form of a pharmaceutical formulation such as in the form of a tablet, pill, sachet or capsule or by tube feeding such as by means of nasogastric, nasoduodenal, esophagostomy, gastrostomy, or jejunostomy tubes, or peripheral or total parenteral nutrition. In another embodiment, the compositions may be administered orally as a dietary supplement.

Compositions for oral administration generally contain inert excipients in addition to the amino acid ingredients of the composition. Oral preparations may be enclosed in gelatin capsules or compressed into tablets. Common excipients used in such preparations include pharmaceutically compatible fillers/diluents such as microcrystalline cellulose, hydroxypropyl methylcellulose, starch, lactose, sucrose, glucose, mannitol, sorbitol, dibasic calcium phosphate, or calcium carbonate; binding agents such as alginic acid, carboxymethylcellulose, microcrystalline cellulose, gelatin, gum tragacanth, or polyvinylpyrrolidone; disintegrating agents such as alginic acid, cellulose, starch, or polyvinylpyrrolidone; lubricants such as calcium stearate, magnesium stearate, talc, silica, or sodium stearyl fumarate; glidants such as colloidal silicon dioxide; sweetening agents such as sucrose or saccharin; flavoring agents such as peppermint, methyl salicylate, or citrus flavoring; coloring agents; and preservatives such as antioxidants (e.g., vitamin A, vitamin C, vitamin E, or retinyl palmitate), citric acid, or sodium citrate. Oral preparations may also be administered as aqueous suspensions, elixirs, or syrups. For these, the active ingredient may be combined with various sweetening or flavoring agents, coloring agents, and, if so desired, emulsifying and/or suspending agents, as well as diluents such as water, ethanol, glycerin, and combinations thereof.

The compositions may be nutritionally complete, i.e. may include other vitamins, minerals, trace elements as well as nitrogen, carbohydrate and fat and/or fatty acid sources so that they may be used as the sole source of nutrition supplying essentially all the required daily amounts of vitamins, minerals, carbohydrates, fat and/or fatty acids, proteins and the like.

(e) Method of Inducing Seizure-Like Activity

Other aspects of the disclosure include a method of inducing seizure-like activity. The method may be used to induce seizure-like activity in vitro by impairing mitochondrial function. In some embodiments, the method of inducing seizures comprises administering a composition that impairs mitochondrial function to a seizure-genic brain region, the hippocampus, in vitro. Non-limiting examples of compositions that may be used to impair mitochondrial function may include rotenone, As2O3, antimycin, cyanide, malonate, 2,4-dinitrophenol (DNP), carbonyl cyanide p-[trifluoromethoxy]-phenyl-hydrazone (FCCP), and oligomycin.

EXAMPLES

The following examples illustrate various iterations of the above disclosure.

Example 1. Bioenergetics are Impaired in Epilepsy

Figure 1:
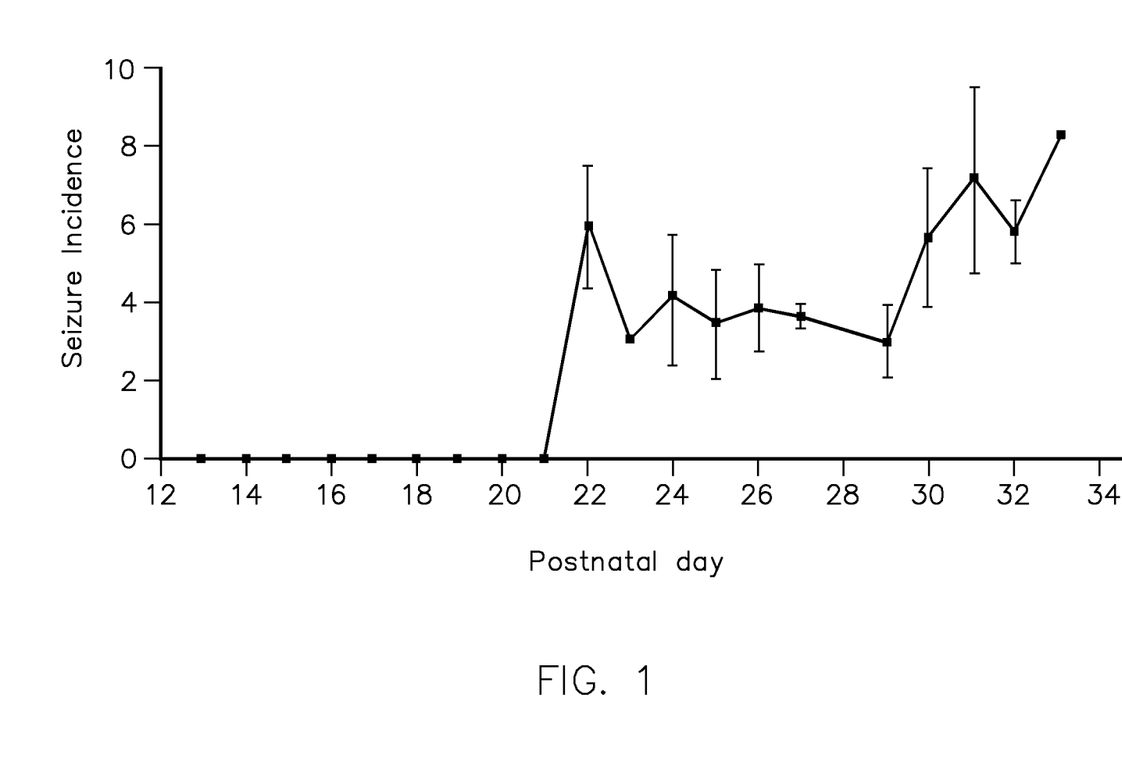
FIG. 1 depicts a graph showing the ontogeny of Kv1.1−/− seizures. On postnatal day (P)10, Kv1.1−/− mice do not exhibit seizures. Around P20, mice experience approximately 3-4 seizures daily. During their P30s, mice experience ~7 seizures per day.
Figure 2:
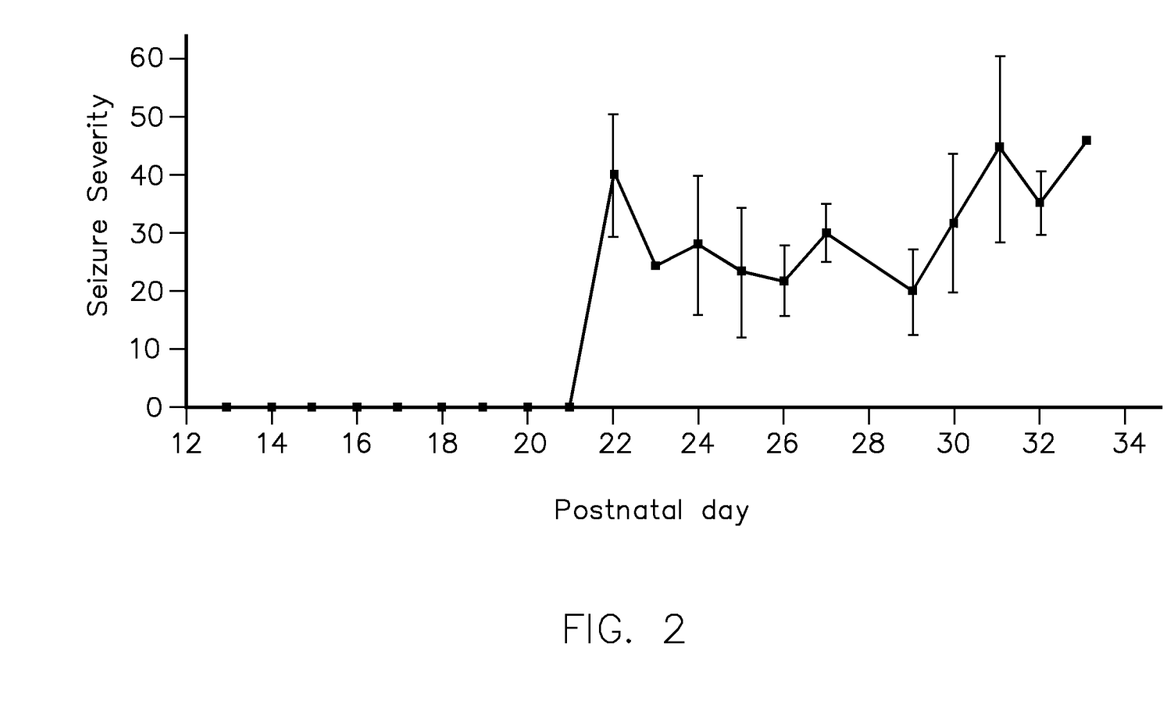
FIG. 2 depicts a graph showing that seizure severity increases with age in Kv1.1−/− mice.

The Kv1.1 knockout mouse naturally develops epilepsy with typical EEG and behavioral seizure manifestations. Seizure onset in the Kv1.1 knockout mouse may occur during the third postnatal week, experiencing 7 seizures each day, with seizure frequency (FIG. 1) and severity (FIG. 2) continuing to increase with age. In these mice, it was found that three mitochondrial functions are impaired in seizure-genic brain regions. Mitochondria are organelles responsible for regulating cellular bioenergetic homeostasis. Due to its high-energy demand and metabolism, brain tissue, and particularly seizure-generating regions such as the hippocampus and cortex, is highly susceptible to impairment of mitochondrial function. Mutations to mitochondrial DNA and impaired mitochondrial respiratory capacity (i.e., energy failure) have been linked to several epilepsy syndromes; thus, deficiencies in cellular and network energy balance are associated with increased probability of hyperexcitable circuits.

Figure 3A:
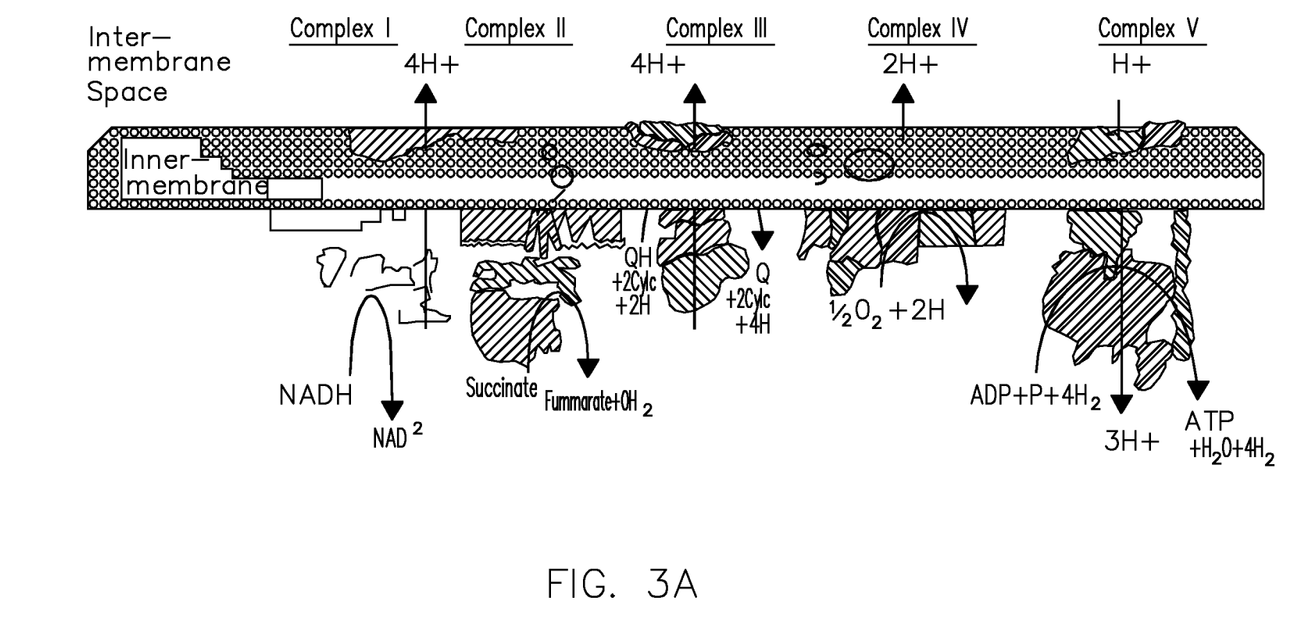
FIG. 3A depicts a schematic of mitochondrial redox and bar graph of impaired mitochondrial function in Kv1.1−/− mice. Polarometric methods monitor complex function and evaluate oxygen consumption via the coupling between transport of electrons thru complex I-IV and ATP synthesis at complex V in control wild-type (WT) and Kv1.1−/− brain tissue.
Figure 3B:
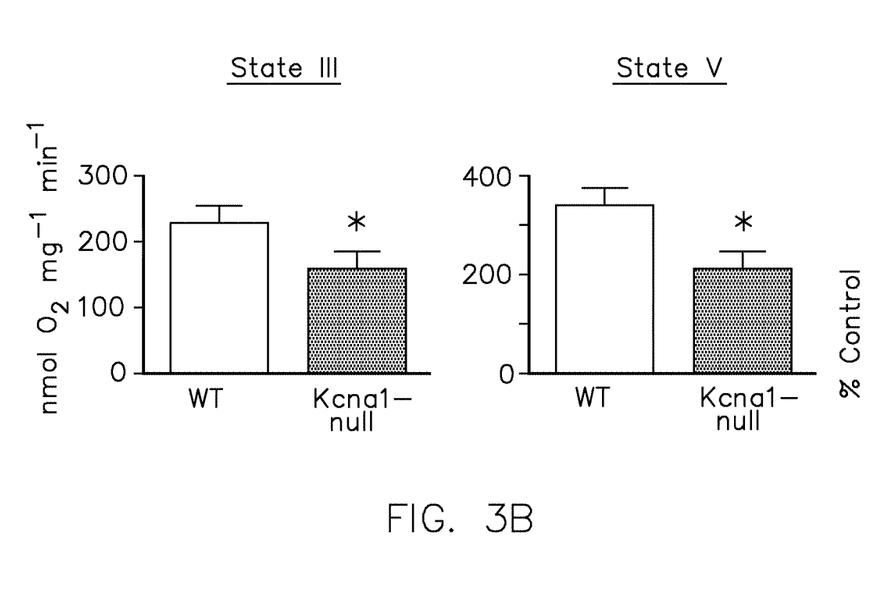
FIG. 3B shows that state III and state V respiratory functions are impaired (i.e. have reduced capacity) in epileptic Kv1.1−/− mice.

Oxidative phosphorylation (redox) occurs at mitochondrial respiratory complexes I-V located in the inner mitochondrial membrane (FIG. 3A). Mitochondrial complex I deficiency has been reported in the temporal lobe of epileptic patients. Functional mitochondrial impairments to proteins in the redox chain can lead to failed transfer of electrons, which then combine with molecular oxygen to form a series of reactive oxygen species (ROS) and nitrogen species. At suprathreshold levels, ROS damages DNA, oxidizes fatty acids in lipids and amino acids in proteins, damages mitochondrial, nuclear and lipid cellular membranes and can mediate mitochondrial permeability transition, which initiates cell injury and death cascades; collectively, interfering with normal bioenergetic homeostasis. In Kv1.1−/− mice, polarographic measurements indicate that complex I-driven state III and state V respiration are significantly reduced in isolated hippocampal and cortical mitochondria (FIG. 3B). This data suggests proteins comprising complex I and V subunits are reduced or damaged. Mitochondria provide a majority of cellular energy in the form of ATP. Reduced state III respiration may produce less ATP. ATP homeostasis helps maintain the neuronal membrane potential and thus is positioned to guard against hyperexcitability.

Figure 3C:
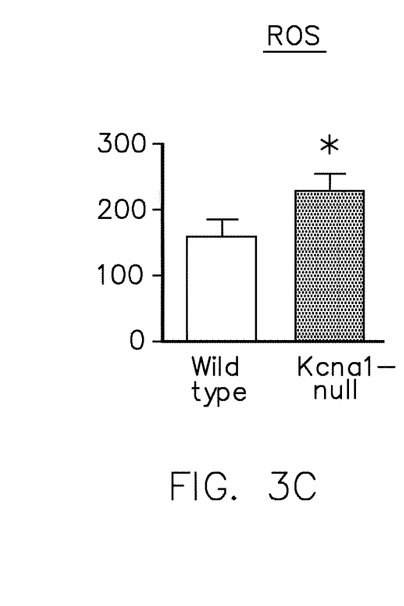
FIG. 3C shows that impaired respiratory function leads to unsuccessful transfer of electrons thru the electron transport chain and, hence, increased production of reactive oxygen species (ROS). n=5-6; * p<0.05.

First, it was discovered that isolated mitochondria from adult Kv1.1−/− mice generate significantly more ROS when compared to wild-type controls (FIG. 3C). It is also shown that ROS production increases during seizures and remains elevated for prolonged periods following seizure cessation. Higher constitutive oxidative stress experienced by the cell under normal conditions, and then exacerbated during seizure events (Kv1.1−/− mice experience ~7 seizures a day), can lead to damaged cellular membranes, proteins/ion channels/receptors, nucleotides (DNA/RNA) and further mitochondrial damage, thus perpetuating cellular bioenergetic imbalance.

Figure 4A:
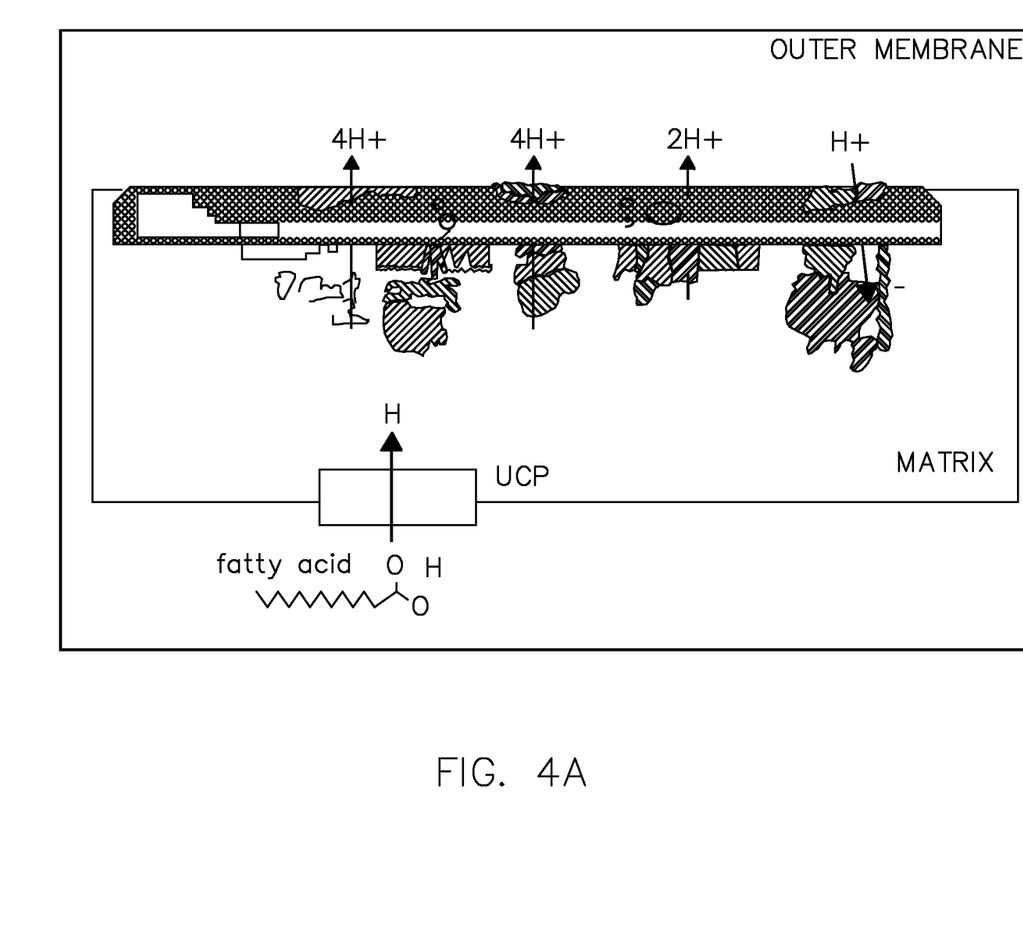
FIG. 4A depicts a schematic of fatty acid (FA, blue)-induced uncoupling.
Figure 4B:
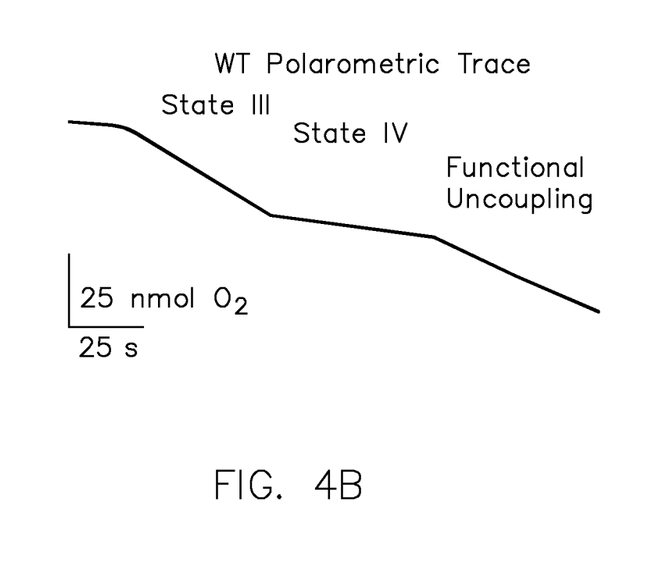
FIG. 4B depicts a polarometric trace of functional uncoupling [i.e. fatty acid-induced respiration following blockade of complex V with oligomycin (state IV)] in wild-type (WT) mitochondria.
Figure 4C:
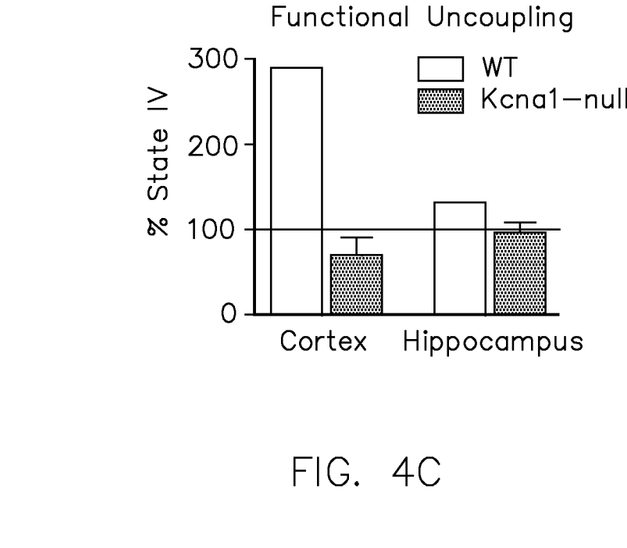
FIG. 4C is a plot showing that Kv1.1−/− mitochondria have limited to no functional uncoupling capacity.

Second, the testing found reduced functional uncoupling in Kv1.1−/− mice (FIGS. 4A-C). In the presence of free fatty acids, mitochondrial uncoupling proteins (UCPs, specifically UCP2 in the brain) translocate protons across the inner membrane back into the matrix (FIG. 4A) to uncouple or release the dependency of the redox chain on complex V (FIG. 4B). This allows for electrons to be successfully transferred, thus reducing ROS and the probability of permeability transition. It has been found that hippocampal mitochondria from rats with kainate-induced seizures have reduced functional uncoupling and enhanced ROS production. In addition, it has been found that acute application of fatty acids functionally uncouples control, but not Kv1.1−/− mitochondria (FIG. 4C). Because in these experiments, complex V is blocked by oligomycin (and therefore fatty-acid induced uncoupling is independent of the redox chain), this data indicates that Kv1.1−/− mitochondria have impaired or reduced expression of UCPs. Uncoupling capacity (i.e. enhanced ability to successfully transfer electrons) helps to withstand seizure-induced hypermetabolic states. Limited uncoupling capacity can result in a significant increase in ROS and cellular injury, thus interfering with bioenergetic homeostasis.

Figure 5A:
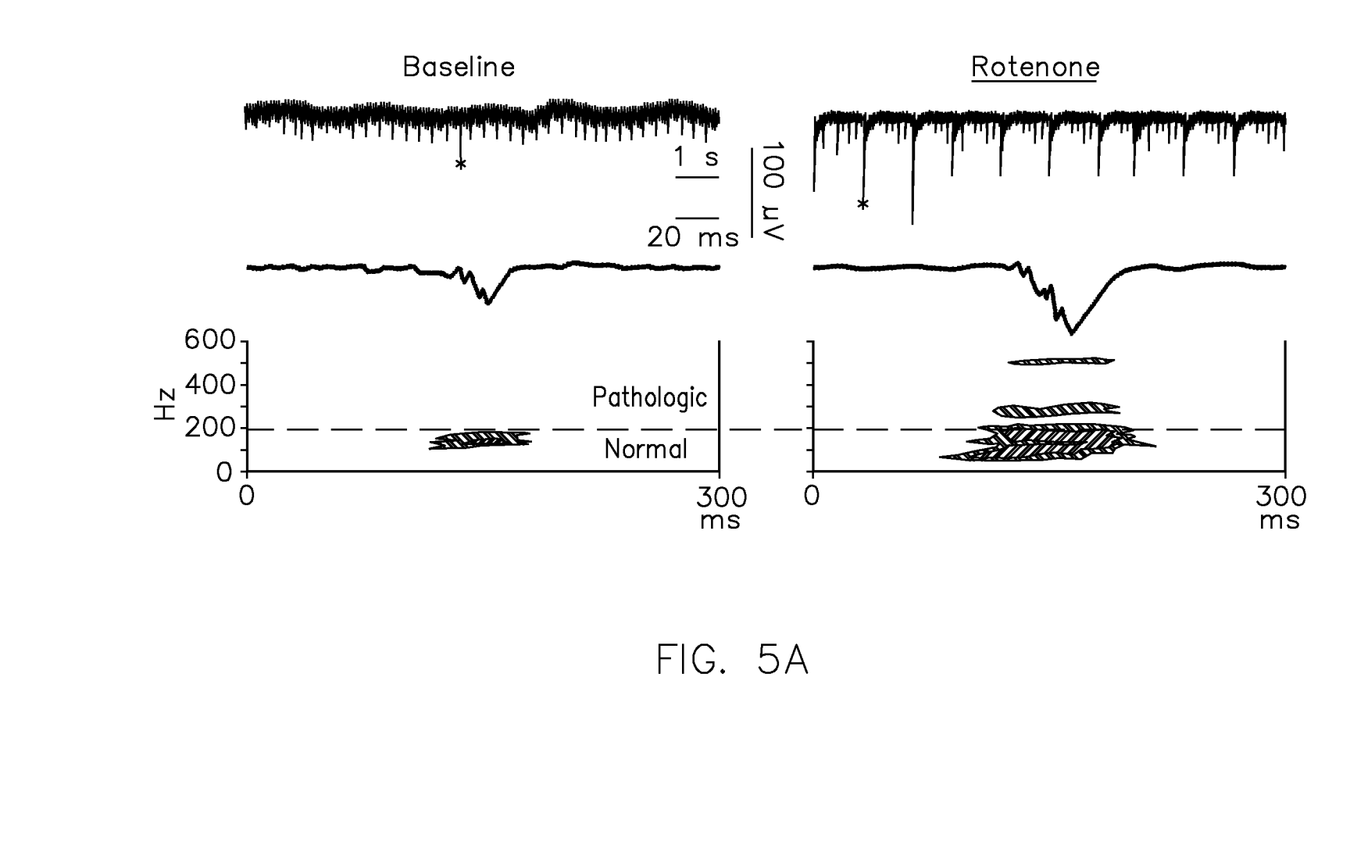
Figure 5B:
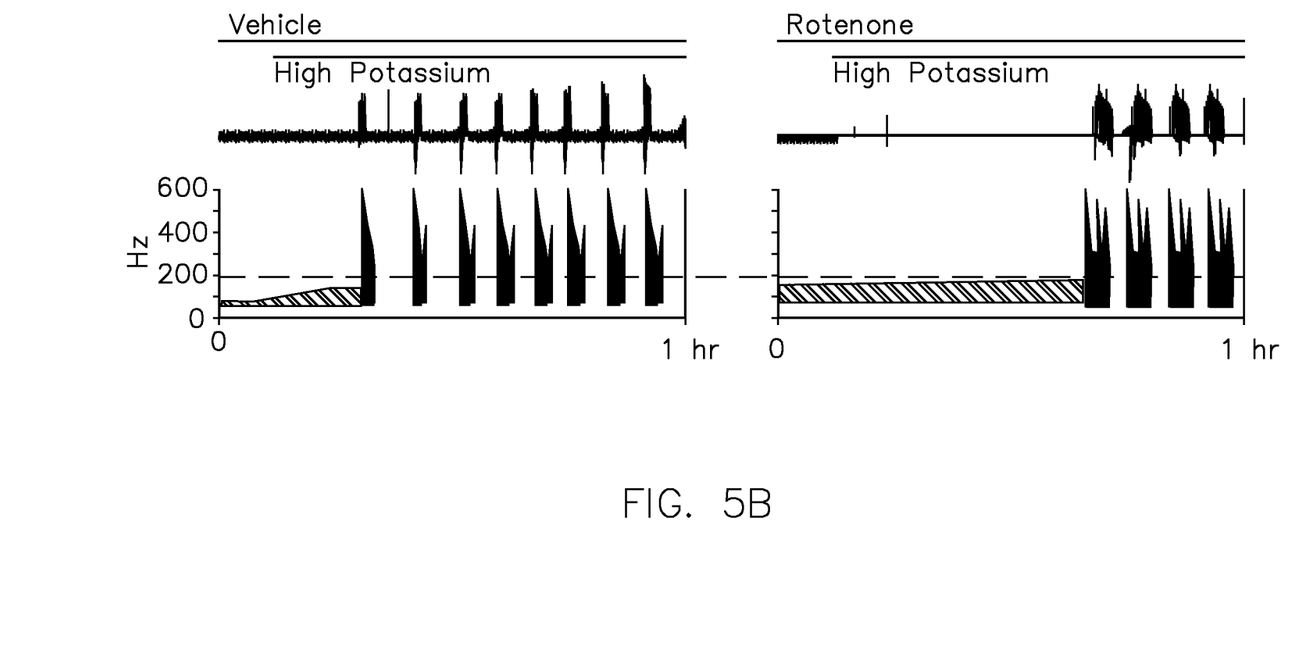
FIG. 5B (Left) shows that increasing the potassium concentration in the artificial cerebral spinal fluid bath solution from 3 mM to 8 mM of a vehicle-treated hippocampal slice increases ripple occurrence, introduces fast ripples and causes regular seizure-like events.

Example 2. Experimentally Impairing Mitochondria in Control Tissue Promotes Seizures Impairing mitochondrial function alone is sufficient to promote seizures. In Kv1.1−/− hippocampal slices, pathological high frequency oscillations are prevalent throughout the in Kv1.1−/− hippocampal network. In addition, there is an increase in neurotransmitter release probabilities at specific hippocampal circuit synapses. To experimentally mimic the mitochondrial pathology seen in epilepsy, a drug that impairs mitochondrial function at respiratory complex I, rotenone, was applied to control tissue. It was found that acute application of rotenone is sufficient to promote seizures (FIG. 5A-B). Specifically, rotenone application promotes spectral disorganization and the generation of pathologic high frequency oscillations (called fast ripples) which reflects a desynchronization of neuronal firing. Fast ripples occur in humans and animals with epilepsy and are biomarkers for seizure-genic foci.

Example 3. Ketogenic Diet and Seizures

In patients with refractory seizures, the ketogenic diet (KD) is effective (specifically against intractable epilepsy and partial and generalized seizures), resulting in complete cessation of seizures in at least 7-10% of patients and >50% reduction in seizure frequency in two-thirds of patients. Unfortunately, particularly in adult patients on the KD, noncompliance is high due to complicated administration regimens, palatability issues and the possibility of side effects due to the high fat content. The efficacy of the KD suggests that it targets a critical and novel anticonvulsant mechanism(s), which is effective against multiple epilepsy syndromes. The fact that seizure control gradually improves over the first few weeks of the KD, indicates that the anticonvulsant constituent of the KD does not merely act on a receptor or ion channel, but may require a longer temporal mechanism of action.

Figure 6A:
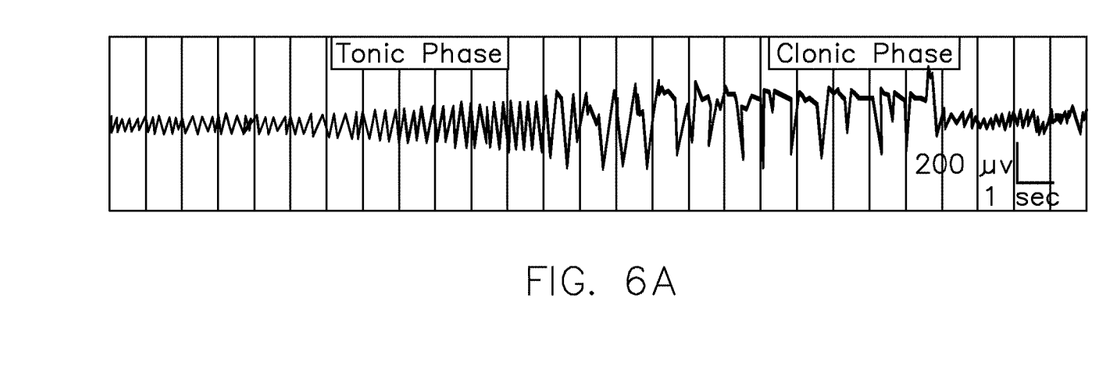
FIG. 6A depicts a trace and bar graphs showing that Ketogenic Diet ("KD") treatment reduces seizures and restores mitochondrial function.
Figure 6B:
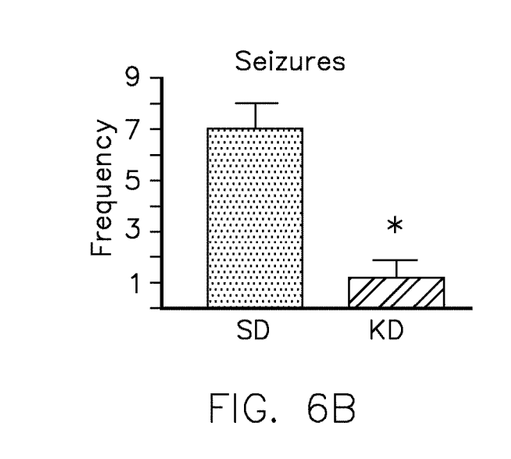
FIG. 6B shows that Kv1.1−/− mice naturally develop epilepsy with typical EEG and behavioral seizure manifestations. KD treatment significantly reduces daily Kv1.1−/− seizures (red bar) when compared to standard diet (SD) controls (black bar); n=5-6, p<0.05.
Figure 6C:
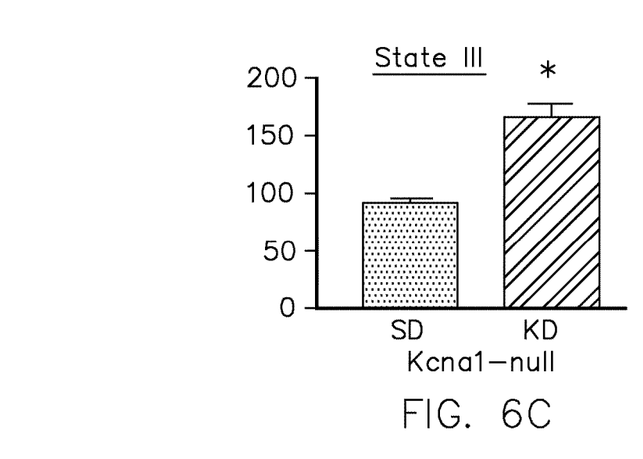
FIG. 6C shows that KD treatment restores mitochondrial function, specifically enhances complex I driven state III respiratory capacity in Kv1.1−/− mice when compared to SD controls; n=5-6, p<0.05.

KD treatment reduces seizures of Kv1.1−/− mice by 75-100% (FIGS. 6A and B). KD treatment is associated with increasing expression of at least 30 bioenergetic proteins, including mitochondrial complex I, II and V, and UCP2, as well as endogenous antioxidants. Two weeks of KD treatment fully restores state III respiration and reduces ROS production in Kv1.1−/− mitochondria to control values (FIG. 6B). In addition, it was found that KD treatment increases UCP expression and function in mitochondria isolated from control and Kv1.1−/− mice (FIG. 6C). Collectively, these data indicate that the KD promotes bioenergetic homeostasis.

Example 4. Restoration of Bioenergetic Homeostasis Alone is Anticonvulsant

Over ninety percent of the caloric intake in the KD is from fat. This high fat:low carbohydrate/protein ratio (3:1 or 4:1) of the KD forces fat catabolism as the primary energy source. Interestingly, fatty acids, specifically long chain polyunsaturated fatty acids, promote bioenergetic homeostasis. Specifically, they are used as metabolic fuels, signaling molecules, increase bioenergetic proteins and ATP production, and improve mitochondrial redox chain function and uncoupling functions. Seizures expend energy and deplete reserve stores, thus compromising cerebral energy balance. Therefore, targeting mechanisms responsible for maintaining energy homeostasis may provide novel anticonvulsant targets.

To that end, a treatment was designed to target specific components of the mitochondria to enhance mitochondrial bioenergetic functions called AATP. AATP comprises pyruvate, vitamin E, and vitamin C. The doses used are: ascorbic acid (vitamin C), 250 mg/kg; sodium pyruvate, 500 mg/kg; tocopherol-succinate (Vitamin E), 30 mg/kg. When administered orally, the doses used were: ascorbic acid (vitamin C), 600 mg/kg; sodium pyruvate, 2.5 g/kg; tocopherol-succinate (Vitamin E), about 75 mg/kg.

Figure 7A:
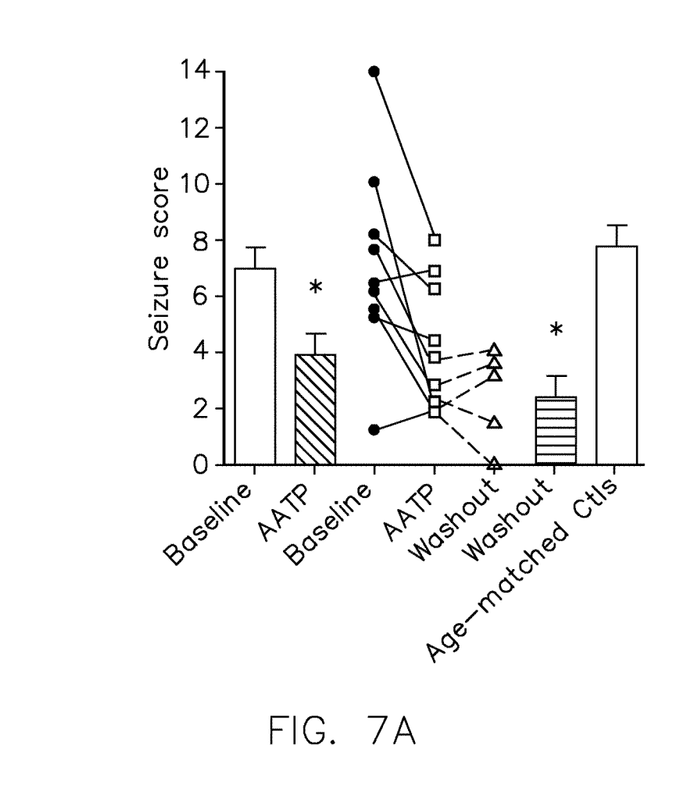
FIG. 7A depicts bar graphs, scatterplots and line graphs showing that targeting mitochondria with AATP is anticonvulsant and antiepileptogenic.
Figure 7B:
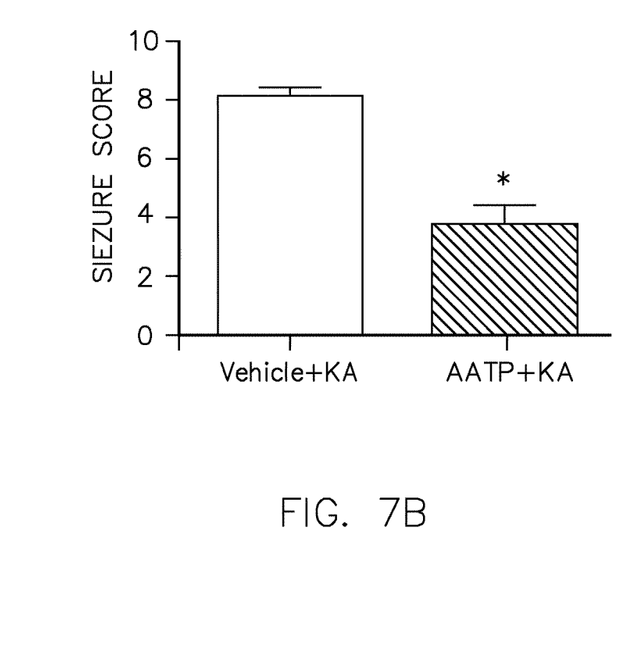
Figure 7C:
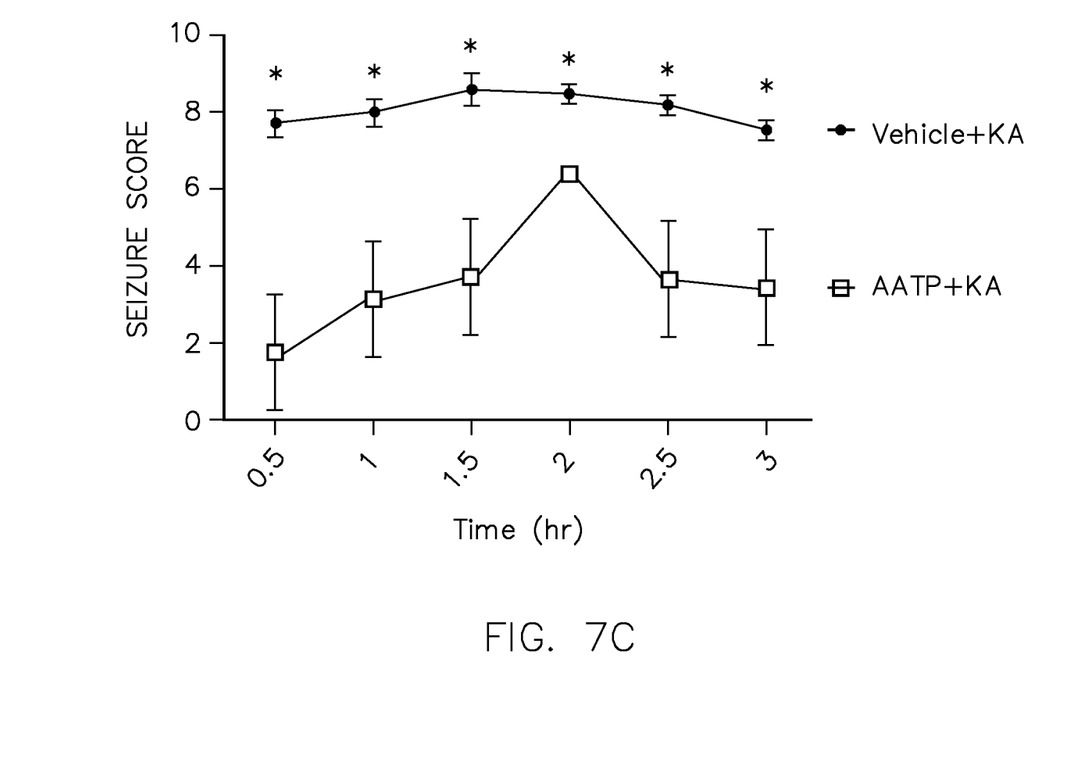
Figure 8A:
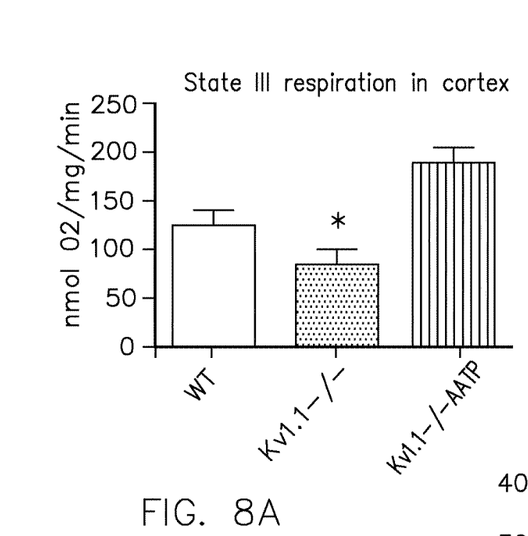
FIGS. 8A-C depict three plots showing that treating Kv1.1−/− mice with AATP completely restores mitochondrial function in Kv1.1−/− mice.
Figure 8B:
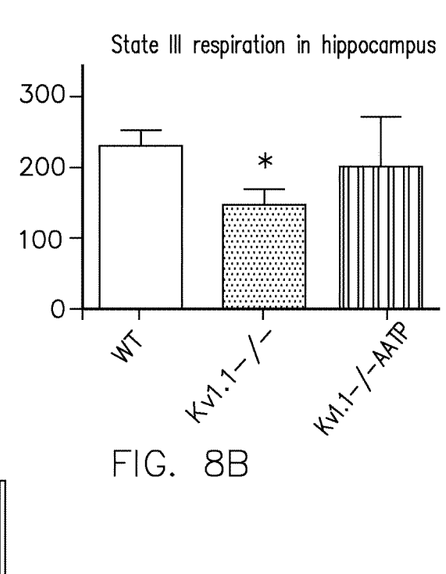
Figure 8C:
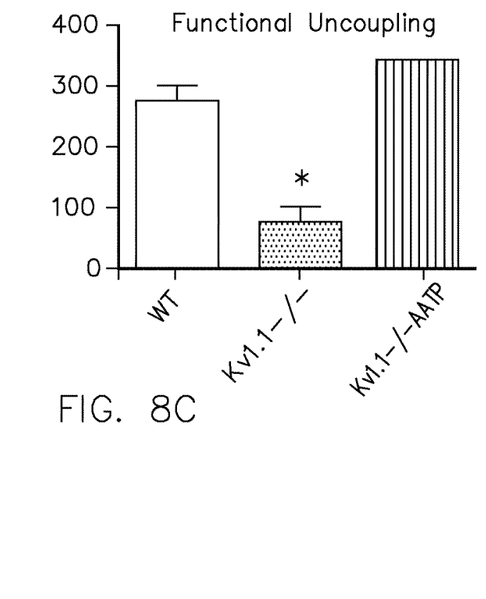

When treated with AATP, seizures induced by kainic acid 30 minutes after treatment with AATP are significant. In vitro, it was found that acute treatment that targets mitochondria is anticonvulsant in epileptic hippocampal slices. Daily treatment of AATP to idiopathic Kv1.1−/− model significantly reduced the onset of epilepsy, or epileptogenesis, seizure frequency and severity (FIG. 7A). Notably, after discontinuation of treatment (washout), seizures remained reduced when compared to age-matched controls. Furthermore, acute AATP treatment was significantly anticonvulsant during the severe state of status epilepticus (FIGS. 7B and C). Furthermore, treating Kv1.1−/− mice with AATP completely restored mitochondrial function in Kv1.1−/− mice in a manner that is similar to the effects of KD, (FIG. 8A-C).

Collectively, the data presented herein indicate that mitochondria impairment is sufficient to promote seizure-genesis and that collective restoration of mitochondrial respiratory, antioxidant and uncoupling functions can be an effective anticonvulsant strategy in epilepsy, particularly for refractory epilepsies.

The invention claimed is:

1. A method of treating seizures, the method comprising administering a composition comprising ascorbic acid, tocotrienol, and pyruvate.

2. The method of claim 1, wherein the composition is configured to be administered orally.

3. The method of claim 1, wherein the composition is configured to be administered intraperitoneally.

4. The method of claim 1, wherein the composition is configured to be administered intravenously.

5. The method of claim 1, wherein 50 mg/kg ascorbic acid, 500 mg/kg pyruvate, and 30 mg/kg tocotrienol are configured to be administered intravenously.

6. The method of claim 1, wherein 600 mg/kg ascorbic acid, 2.5 g/kg pyruvate, and 75 mg/kg tocotrienol are configured to be administered orally.

7. The method of claim 1, wherein the seizure is a status epilepticus seizure.

8. The method of claim 1, wherein the seizure-genic brain region is the hippocampus or cortex.

9. The method of claim 1, wherein mitochondrial function is selected from the group consisting of respiratory, antioxidant, uncoupling functions of the mitochondria, and a combination thereof.

10. A composition comprising a combination of ascorbic acid, pyruvate, and tocotrienol, wherein the ratio of ascorbic acid to tocotrienol is between about 1:6 and about 1:10, the ratio of ascorbic acid to pyruvate is between about 1:1.5 and about 1:4.5, and the ratio of tocotrienol to pyruvate is between about 1:12 and about 1:40.

11. The composition of claim 10, wherein the composition is formulated for oral administration.

12. The composition of claim 10, wherein the composition is formulated for IV administration.

13. The composition of claim 10, wherein the ratio of ascorbic acid to tocotricnol is between about 1:7 and about 1:9.

14. The composition of claim 10, wherein Ihe ratio of ascorbic acid to pyruvate is about 1:2.

15. The composition of claim 10, wherein the ratio of ascorbic acid to pyruvate is about 1:4.

16. The composition of claim 10, wherein the ratio of tocotrienol to pyruvate is about 1:16.

17. The composition of claim 10, wherein the ratio of tocotrienol to pyruvate is about 1:33.

\* \* \* \* \*